United States Patent [19]

Murayama et al.

[11] 4,076,835
[45] Feb. 28, 1978

[54] ESTER OF CHRYSANTHEMIC ACID, PROCESS FOR THE PREPARATION THEREOF AND INSECTICIDAL COMPOSITIONS CONTAINING THEM

[75] Inventors: Keisuke Murayama; Motoji Asai; Hideakira Tsuji, all of Tokyo, Japan

[73] Assignee: Sankyo Company Limited, Tokyo, Japan

[21] Appl. No.: 640,229

[22] Filed: Dec. 12, 1975

Related U.S. Application Data

[60] Division of Ser. No. 292,262, Sep. 25, 1972, abandoned, which is a continuation of Ser. No. 42,450, Jun. 1, 1970, abandoned.

[30] Foreign Application Priority Data

Jun. 2, 1969   Japan ................................. 44-43143
Aug. 16, 1969   Japan ................................. 44-64809

[51] Int. Cl.$^2$ ............................................. A01N 9/28
[52] U.S. Cl. ................................. 424/285; 260/346.22
[58] Field of Search .................. 424/285; 260/346.2 R

[56] References Cited

U.S. PATENT DOCUMENTS 3,567,740  2/1971  Matsui et al. ..................... 260/347.4
3,976,663  8/1976  Fanta ..................................... 424/285

Primary Examiner—Allen J. Robinson
Attorney, Agent, or Firm—Toren, McGeady and Stanger

[57] ABSTRACT

A new ester of chrysanthemic acid having the formula

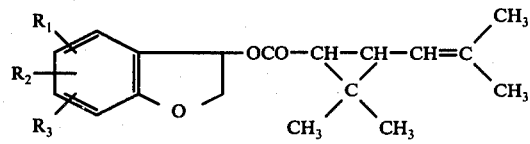

wherein $R_1$, $R_2$ and $R_3$ are the same or different and each represents a hydrogen atom, a lower alkyl group or a halogen atom which exhibits insecticidal activity. The ester is prepared by reacting a 2,3-dihydro-3-benzofuranol derivative having the formula

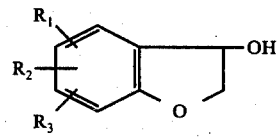

wherein $R_1$, $R_2$ and $R_3$ are the same as above with chrysanthemic acid or an active ester thereof such as the halogenide and the anhydride.

2 Claims, No Drawings

ESTER OF CHRYSANTHEMIC ACID, PROCESS FOR THE PREPARATION THEREOF AND INSECTICIDAL COMPOSITIONS CONTAINING THEM

CROSS REFERENCE TO RELATED APPLICATIONS

This application is a Divisional Application of prior application Ser. No. 292,262, filed on Sept. 25, 1972, now abandoned, which, in turn, was a Continuation of Ser. No. 42,450, filed on June 1, 1970, now abandoned.

This invention relates to novel esters of chrysanthemic acid having the formula

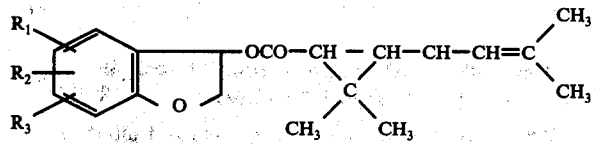

wherein $R_1$, $R_2$ and $R_3$ are the same or different and each represents a hydrogen atom, a lower alkyl group or a halogen atom, a process for the preparation of said esters and insecticidal compositions containing said esters as the active ingredient.

It has long been known that synthetic products having a basic structural similarity to pyrethrins which are esters of chrysanthemic acid exhibit insecticidal activity of significant order. One of these synthetic pyrethroids is known as allethrin. However, there have been desired synthetic insecticides having higher toxicity to insects and lower mammalian toxicity. As a resulting of earnest studies to insecticidal activity of various esters of chrysanthemic acid, we have found that the novel esters having the formula (I) exhibit higher insecticidal activity against not only pests of sanitary importance such as mosquito, house fly and mite, but also plant pests such as plant hopper, leaf hopper and aphid, as compared with allethrin. Furthermore, the esters of this invention exhibit very low toxicity to mammalian and have a feature that it may be more safely employed.

It is therefore an object of this invention to provide novel esters of chrysanthemic acid (I) suitable for use as an insecticide and a process for the preparation of said compounds. It is another object of this invention to provide insecticidal compositions containing as an active ingredient at least one of the aforesaid compounds. Other objects of this invention will be apparent from the following detailed description.

The esters of chrysanthemic acid of this invention are novel compounds unknown in the prior art and may be prepared by a process which comprises reacting a 2,3-dihydro-3-benzofuranol derivative having the formula

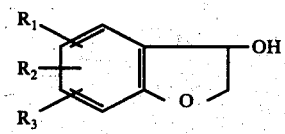

wherein $R_1$, $R_2$ and $R_3$ are the same as above with chrysanthemic acid or an active ester thereof. The active esters as used herein include an acid halogenide, an acid anhydride and a lower alkyl ester of chrysanthemic acid. The 2,3-dihydro-3-benzofuranol derivatives (II) employed as starting materials in this invention are prepared by reducing the corresponding 3(2H)-benzofuranone derivative with a reducing agent such as lithium aluminium hydride and sodium boron hydride.

The reaction in this invention is an esterification reaction and may be carried out by various methods as follows;

1. When the 2,3-dihydro-3-benzofuranol derivative (II) is reacted with a chrysanthemic acid halide preferably the chloride, the reaction is conducted in the presence or absence of an inert solvent such as benzene and toluene with addition of an organic base such as pyridine, triethylamine and methylpyperidine or a weakly basic inorganic salt such as potassium carbonate as an acid binding agent. The reaction temperature is not limited, but preferably at room temperature or below.

2. When the 2,3-dihydro-3-benzofuranol derivative (II) is reacted with chrysanthemic acid, they are heated under reflux in an inert solvent such as benzene or toluene in the presence of a dehydrating catalyst such as sulfuric acid and p-toluenesulfonic acid while the water produced during the reaction is distilled off, or they are heated under reflux in said solvent in the presence of tosyl chloride and an organic base such as pyridine and triethylamine.

3. When the 2,3-dihydro-3-benzofuranol derivative (II) is reacted with a lower alkyl ester of chrysanthemic acid, they are heated in the presence of a transesterification catalyst such as sodium methylate while the lower alcohol produced during the reaction is distilled off.

4. When the 2,3-dihydro-3-benzofuranol derivative (II) is reacted with chrysanthemic acid anhydride, they are heated under reflux in an inert solvent. After completion of the reaction, the desired product is recovered by a conventional means. For example, the reaction mixture is washed with dilute hydrochloric acid, aqueous sodium bicarbonate and aqueous saturated sodium chloride successively. The organic solvent layer is separated and dried over anhydrous sodium sulfate. The solvent is distilled off from the dried solution. The residue is subjected to high vacuum distillation or column chromatography. As illustrative of the esters (I) of this invention are given the following compounds;

| Compound No. | esters of chrysanthemic acid of this invention | physical property |
|---|---|---|
| 1 | 2,3-DIhydro-3-benzofuranyl chrysanthemate | B.P.115–121° C./ 0.02 mmHg. |
| 2 | 2,3-Dihydro-4-methyl-3-benzofuranyl chrysanthemate | B.P.125–127° C./ 0.01 mmHg. |
| 3 | 2,3-Dihydro-5-methyl-3-benzofuranyl chrysanthemate | B.P.119–122° C./ 0.05 mmHg. |
| 4 | 2,3-Dihydro-6-methyl-3-benzofuranyl chrysanthemate | B.P.120–122° C./ 0.01 mmHg. |
| 5 | 2,3-Dihydro-7-methyl-3-benzofuranyl chrysanthemate | B.P.112–116° C./ 0.08 mmHg. |
| 6 | 2,3-Dihydro-5-ethyl-3-benzofuranyl chrysanthemate | B.P.130–132° C./ 0.01 mmHg. |
| 7 | 2,3-Dihydro-5-chloro-3-benzofuranyl chrysanthemate | B.P.117–122° C./ 0.06 mmHg. |
| 8 | 2,3-Dihydro-4,6-dimethyl-3-benzofuranyl chrysanthemate | B.P.130–133° C./ 0.02 mmHg. |
| 9 | 2,3-Dihydro-5,7-dimethyl-3-benzofuranyl chrysanthemate | B.P.133–136° C./ 0.03 mmHg. |
| 10 | 2,3-Dihydro-5,7-dichloro-3-benzofuranyl chrysanthemate | B.P.140–145° C./ 0.005 mmHg. |
| 11 | 2,3-Dihydro-4,6,7-trimethyl-3- | B.P.135–139° C./ |

-continued

| Compound No. | esters of chrysanthemic acid of this invention | physical property |
|---|---|---|
|  | benzofuranyl chrysanthemate | 0.01 mmHg. |
| 12 | 2,3-Dihydro-4,6-dimethyl-5-chloro-3-benzofuranyl chrysanthemate | B.P.142–145° C./ 0.005 mmHg. |
| 13 | 2,3-Dihydro-7-chloro-3-benzofuranyl chrysantehmate | B.P.121–123° C./ 0.001 mmHg. |
| 14 | 2,3-Dihydro-5-tert. butyl-3-benzofuranyl chrysanthemate | B.P.137–140° C./ 0.005 mmHg. |

In formulating the esters (I) of this invention into the insecticidal composition, there may be prepared any of the various forms including dusts, wettable powders, emulsions, oils, granules, aerosols, fumigants, mosquito coils and the like, by way of a conventional technique known to those skilled in the art. In the preparation of the insecticidal compositions, there may be employed an inert solid carrier such as talc, clay, bentonite and diatomaceous earth, a liquid carrier such as benzene, xylene, acetone, solvent naphtha and kerosene and an adjuvant such as a surfactant.

The present composition may contain known pyrethrum synergists such as piperonyl butoxide and piperonyl sulfoxide for the purpose of promoting effectiveness of the active ingredient. And also the present composition may be in admixture with organic chlorinated insecticides such as B.H.C. and D.D.T., phenitrothion, malathion, dichlorvos, trichlorfon, pyrethrum extracts, other pyrethroids such as allethrin, various acaricides, various faliar fertilizers or plant growth regulators.

The insecticidal composition of this invention may be applied to harmful insects or their living place with a conventional means, for example, to such harmful insects by direct-spraying or to such place by spraying, painting, fogging or fumigating. The results of tests on the insecticidal activities of the composition according to this invention are shown below.

1. Knock-down effect against female adult house flies

The above-listed compounds (No. 1– 14) are dissolved in acetone, respectively. 15 female adult house flies are placed in a glass vial having a diameter of 9 cm. and a height of 6 cm. covered with wire-netting. The acetone solution is sprayed to the glass vials in an amount of 0.6 ml per glass vial. Two experiments are conducted at each concentration. Knock-down percent of individuals after 20 minutes are listed in the Table 1 below.

Table 1.

| Amount of the active compound per glass vial | Knock-down per cent | | | |
|---|---|---|---|---|
| Compound No. | 7.7mg. | 0.77mg. | 0.077mg. | 0.0077mg. |
| 1 | 100 | 100 | 100 | 6.6 |
| 2 | 100 | 100 | 83.3 | 0 |
| 3 | 100 | 100 | 100 | 6.6 |
| 4 | 100 | 100 | 96.6 | 10.0 |
| 5 | 100 | 100 | 100 | 23.3 |
| 6 | 100 | 100 | 90.0 | 0 |
| 7 | 100 | 100 | 83.3 | 10.0 |
| 8 | 100 | 100 | 83.3 | 0 |
| 9 | 100 | 100 | 86.6 | 0 |
| 10 | 100 | 100 | 83.3 | 0 |
| 11 | 100 | 100 | 80.0 | 0 |
| 12 | 100 | 100 | 80.0 | 0 |
| 13 | 100 | 100 | 100 | 23.3 |
| 14 | 100 | 100 | 100 | 6.6 |

2. Knock-down effect against adult of mosquito (Culex pipiens molestus)

The listed compounds (No. 1 – 14) and allethrin are mixed with a base for mosquito coil and the mixture is formulated to mosquito coil by a conventional means. The coils are fired for 5 minutes in a box (45 × 45 × 60 cm.) in vhich 20 of adults of mosquito are placed previously. The number of the knock-down flies are examined at the given intervals of time. The results are listed in the Table 2 below.

Table 2.

| Compound No. | Knock-down per cent of mosquitos | | |
|---|---|---|---|
|  | 2 min. | 4 min. | 8 min. |
| 1 | 5 | 10 | 100 |
| 2 | 10 | 35 | 100 |
| 3 | 5 | 10 | 100 |
| 4 | 10 | 15 | 100 |
| 5 | 10 | 35 | 100 |
| 6 | 0 | 15 | 100 |
| 7 | 5 | 15 | 100 |
| 8 | 0 | 15 | 100 |
| 9 | 0 | 20 | 100 |
| 10 | 0 | 10 | 100 |
| 11 | 0 | 10 | 100 |
| 12 | 0 | 10 | 100 |
| 13 | 10 | 35 | 100 |
| 14 | 5 | 10 | 100 |
| allethrin | 15 | 25 | 100 |

3. Insecticidal activities against larval mosquitos (Culex pipiens molestus)

300 ml. of water is placed in a glass vial having a diameter of 7.5 cm. and a height of 9 cm. and 10 larval mosquitos are placed in the glass vial. One ml. of the acetone solution containing an active compound is added to the glass vial. Mortalities of said insects are examined at the given intervals of time. Two experiments are conducted at each concentration.
The results are listed in the Table 3 below.

Table 3.

| Compound | Mortalities (%) (Including know-down individuals) | | | | | |
|---|---|---|---|---|---|---|
|  | Concentration p.p.m. | 30 min. | 1 hr. | 2 hrs. | 3 hrs. | 24 hrs. |
| 2,3-Dihydro-3-benzofuranyl chrysanthemate | 1 | 100 | 100 | 100 | 100 | 100 |
|  | 0.1 | 25 | 85 | 100 | 100 | 100 |
|  | 0.01 | 0 | 0 | 0 | 0 | 0 |
| 2,3-Dihydro-7-methyl-3-benzofuranyl chrysanthemate | 1 | 100 | 100 | 100 | 100 | 100 |
|  | 0.1 | 70 | 100 | 100 | 100 | 100 |
|  | 0.01 | 0 | 0 | 0 | 0 | 0 |
| 2,3-Dihydro-4,6-dimethyl-3-benzofuranyl chrysanthemate | 1 | 100 | 100 | 100 | 100 | 100 |
|  | 0.1 | 10 | 50 | 85 | 100 | 100 |
|  | 0.01 | 0 | 0 | 0 | 0 | 0 |
| 2,3-Dihydro-4,6-dimethyl-5-chloro-benzofuranyl | 1 | 100 | 100 | 100 | 100 | 100 |
|  | 0.1 | 30 | 75 | 100 | 100 | 100 |
|  | 0.01 | 0 | 0 | 0 | 0 | 0 |

Table 3.-continued

| Compound | Concentration p.p.m. | Mortalities (%) (Including know-down individuals) | | | | |
|---|---|---|---|---|---|---|
| | | 30 min. | 1 hr. | 2 hrs. | 3 hrs. | 24 hrs. |
| chrysanthemate | | | | | | |
| 2,3-Dihydro-7- | 1 | 100 | 100 | 100 | 100 | 100 |
| chloro-3-benzo- | 0.1 | 40 | 80 | 100 | 100 | 100 |
| furanyl chrysan- | 0.01 | 0 | 0 | 0 | 0 | 5 |
| themate | | | | | | |
| allethrin | 1 | 75 | 100 | 100 | 100 | 100 |
| | 0.1 | 0 | 15 | 40 | 55 | 65 |
| | 0.01 | 0 | 0 | 0 | 0 | 0 |
| Non-treated | acetone | 0 | 0 | 0 | 0 | 0 |

In order that the invention may be better understood, the following examples are given, and it should be understood that these are given for illustration but not for limitation of the scope of the invention.

EXAMPLE 1

0.02 mole of 2,3-dihydro-3-benzofuranol and 0.03 mole of dry pyridine are dissolved in 25 ml. of dry toluene and the resulting solution is cooled below 10° C. To the solution is added dropwise 0.02 mole of chrysanthemic acid chloride in 10 ml. of dry toluene with stirring. After the reaction mixture is allowed to stand overnight at room temperature under protection against moisture, it is washed with aqueous dilute hydrochloric acid, aqueous sodium hydrogencarbonate and aqueous saturated sodium chloride successively. The organic solvent layer is separated and dried over anhydrous sodium sulfate. The solvent is distilled off from the dried solution and the residue is subjected to distillation in high vacuum to give 2,3-dihydro-3-benzofuranyl chrysanthemate.

B.P. 115–121° C./0.02 mmHg.
I.R. (liquid film) $vc = o$   1726 cm$^{-1}$
Analysis:
Calc'd. for $C_{18}H_{22}O_3$;   C, 75.49%; H, 7.74%;
Found;   C, 75.84%; H, 8.15%.

In the same manner as above, the following compounds are prepared;

2,3-dihydro-5-methyl-3-benzofuranyl chrysanthemate
B.P. 119–122° C./0.05 mmHg.
I.R. (liquid film) $vc = o$   1726 cm$^{-1}$
2,3-dihydro-7-methyl-3-benzofuranyl chrysanthemate,
B.P. 112–116° C./0.08 mmHg.
I.R. (liquid film) $vc = o$   1729 cm$^{-1}$
2,3-dihydro-5-chloro-3-benzofuranyl chrysanthemate,
B.P. 117–122° C./0.06 mmHg.
I.R. (liquid film) $vc = o$   1722 cm$^{-1}$

EXAMPLE 2

To the solution of 0.05 mole of 2,3-dihydro-7-methyl-3-benzofuranol and 0.05 mole of chrysanthemic acid in 100 ml. of dry benzene is added 0.5 g. of p-toluenesulfonic acid and the resulting mixture is heated under reflux while the water produced during the reaction is distilled off. After completion of the distillation of water, the reaction mixture is treated with the same procedure as in Example 1, but replacing the distillation with alumina- or silica gel chromatography to give 2,3-dihydro-7-methyl-benzofuranyl chrysanthemate.

B.P. 112–116° C/0.08 mmHg.
I.R. $vc = o$   1729 cm$^{-1}$
Analysis;
Calc'd for $C_{19}H_{24}O_3$;   C,75.97%; H,8.05%

-continued
Found;   C,75.65%; H,8.01%

EXAMPLE 3

To 0.02 mole of 2,3-dihydro-3-benzofuranol are added 0.021 mole of methyl chrysanthemate and 0.01 mole of sodium methylate and the resulting mixture is heated at about 100° C. While the methanol produced during the reaction is distilled off.

After completion of the distillation of methanol, the reaction mixture is extracted with ether and the ether extract is treated with the same procedure as in Example 1 to give 2,3-dihydro-3-benzofuranyl chrysanthemate.

B.P. 115–121° C./0.02 mmHg.
I.R. (liquid film) $vc = o$   1726 cm$^{-1}$
Analysis;
Calc'd for $C_{18}H_{22}O_3$;   C,75.49%; H,7.74%
Found;   C,75.68%; H,7.97%

EXAMPLE 4

0.02 mole of 2,3-dihydro-3-benzofuranol and 0.021 mole of chrysanthemic acid anhydride are dissolved in 25 ml. of dry benzene and the resulting solution is heated under reflux for 3 hours. After the reaction mixture is allowed to cool, it is treated with the same procedure as in Example 1 to give 2,3-dihydro-3-benzofuranyl chrysanthemate.

B.P. 115–121° C./0.02 mmHg.
I.R. (liquid film) $vc = o$   1726 cm$^{-1}$
Analysis;
Calc'd for $C_{18}H_{22}O_3$;   C,75.94%; H,7.74%
Found;   C,75.84%; H,8.15%.

The following Examples 5 – 8 illustrate typical insecticidal compositions of this invention.

EXAMPLE 5

One part by weight of 2,3-dihydro-3-benzofuranyl chrysanthemate is dissolved in 20 parts by weight of acetone and to the resulting solution is added 99 parts by weight of diatomaceous earth of 300 mesh. The mixture is thoroughly stirred and the acetone is evaporated to give a dust composition.

EXAMPLE 6

The emulsions are prepared by mixing the following components;

| Component | Parts by weight |
|---|---|
| 2,3-dihydro-5-chloro-3- | |

-continued

| Component | Parts by weight |
|---|---|
| benzofuranyl chrysanthemate | 10 |
| Paracol* | 10 |
| xylene | 80 |

*Trade name of the surface active agent manufactured and sold by Nippon Nyukazai Co., Ltd. Japan.

EXAMPLE 7

The aerosols are prepared by charging the following components into a conventional aerosol vessel in a usual manner.

| Component | Parts by weight |
|---|---|
| 2,3-dihydro-7-methyl-3-benzofuranyl chrysanthemate | 0.4 |
| pyrethrum extract | .0.5 |
| piperonyl butoxide | 1.5 |
| lindane | 1.0 |
| xylene | 5 |

-continued

| Component | Parts by weight |
|---|---|
| kerosene | 5.6 |
| freon | 86 |

EXAMPLE 8

0.5 g. of 2,3-dihydro-7-methyl-3-benzofuranyl chrysanthemate is dissolved in 30 ml. of acetone and the resulting solution is admixed with 99 g. of a conventional carrier for mosquito coil. The acetone is evaporated from the mixture and the residue is kneaded with 100 ml. of water, shaped and dried to give mosquito coil containing 0.5% of active ingredient.

What is claimed is:

1. An insecticidal composition comprising an insecticidally effective amount of 2,3-dihydro-7-methyl-3-benzofuranyl chrysanthemate and a compatible carrier.

2. A method for combatting harmful insects which comprises applying an insecticidally effective amount of 2,3-dihydro-7-methyl-3-benzofuranyl chrysanthemate to said insects.

* * * * *